(12) United States Patent
Shepard et al.

(10) Patent No.: US 7,186,981 B2
(45) Date of Patent: *Mar. 6, 2007

(54) METHOD AND APPARATUS FOR THERMOGRAPHIC IMAGING USING FLASH PULSE TRUNCATION

(75) Inventors: Steven M. Shepard, Southfield, MI (US); Timothy Young, Oak Park, MI (US)

(73) Assignee: Thermal Wave Imaging, Inc., Ferndale, MI (US)

( * ) Notice: Subject to any disclaimer, the term of this patent is extended or adjusted under 35 U.S.C. 154(b) by 76 days.

This patent is subject to a terminal disclaimer.

(21) Appl. No.: 10/902,225

(22) Filed: Jul. 29, 2004

(65) Prior Publication Data

US 2005/0056786 A1 Mar. 17, 2005

Related U.S. Application Data

(60) Provisional application No. 60/490,674, filed on Jul. 29, 2003, provisional application No. 60/490,880, filed on Jul. 29, 2003.

(51) Int. Cl.
*G01N 21/00* (2006.01)
(52) U.S. Cl. .................. 250/341.1; 702/82; 250/338.1
(58) Field of Classification Search ............. 250/341.1; 702/82
See application file for complete search history.

(56) References Cited

U.S. PATENT DOCUMENTS 4,878,116 A * 10/1989 Thomas et al. ............. 348/619
5,041,726 A * 8/1991 Chang et al. ............. 250/341.8
6,712,502 B2 * 3/2004 Zalameda et al. ............. 374/5
6,795,784 B1 * 9/2004 Shepard ....................... 702/82
6,937,331 B1 * 8/2005 Nguyen ....................... 356/305
2003/0027186 A1 * 2/2003 Pierce ........................... 435/6
2005/0018748 A1 * 1/2005 Ringermacher et al. .... 374/121
2005/0190259 A1 * 9/2005 Mitsuhashi et al. ........... 348/87

FOREIGN PATENT DOCUMENTS

JP 54153641 A * 12/1979
WO WO9944399 * 9/1999

* cited by examiner

*Primary Examiner*—Renee Luebke
*Assistant Examiner*—Mary Zettl
(74) *Attorney, Agent, or Firm*—Honigman, Miller, Schwartz and Cohn LLP

(57) ABSTRACT

A pulse controller device for controlling the excitation of a heat source used in thermographic imaging is disclosed. The pulse controller device comprises a power supply, a heat source coupled to the power supply, a device coupled to the power supply signaling the power supply to deliver electrical power to the heat source, a sensor for sensing the delivery of electrical power to the heat source, a flash duration module coupled to said sensor for measuring a duration of time, and a gate device coupled to said flash duration module for gating the electrical power utilized by the heat source. A method for thermographically evaluating a sample is also disclosed.

31 Claims, 9 Drawing Sheets

METHOD AND APPARATUS FOR THERMOGRAPHIC IMAGING USING FLASH PULSE TRUNCATION

RELATED APPLICATION INFORMATION

The present invention is related to provisional patent application Ser. Nos. 60/490,674 and 60/490,880, both filed on Jul. 29, 2003.

BACKGROUND OF THE INVENTION

1. Field of the Invention

The present invention generally relates to thermographic imaging and more particularly relates to pulsed thermography.

2. Description of the Related Art

Active thermography is used to nondestructively evaluate (NDE) samples for sub-surface defects. It is effective for uncovering internal bond discontinuities, delaminations, voids, inclusions, and other structural defects that are not detectable by visual inspection of the sample. Generally, active thermography involves heating or cooling the sample to create a difference between the sample temperature and the ambient temperature and then observing the infrared thermal signature that emanates from the sample as its temperature returns to ambient temperature. In application, pulsed thermography NDE is widely used in evaluating, for example, aerospace and power generation industry devices.

An infrared (IR) camera is typically used for thermography because it is capable of detecting anomalies in the cooling behavior of the sample are commonly caused by sub-surface defects blocking the diffusion of heat from the surface of the sample surface to the sample's interior. More particularly, subsurface defects cause the surface immediately above the defect to cool at a different rate than that of the surrounding defect-free areas. As the sample cools, the IR camera captures and records an image of the sample, creating a sequential time record of the sample's surface temperature.

Systems for thermographic heating typically employ xenon flashtubes and off-the-shelf photographic power supplies for sample excitation. In an alternative embodiment, a laser may be employed to heat a surface; however, lasers are less practical when used to instantaneously heat a large area. The use of commercial off-the-shelf power supplies is extremely convenient, cost effective, and safe.

Off-the-shelf flashlamps (and their associated power supplies which provide current pulses with energies on the order of 3–6 kJoules) are used to generate a plasma arc in a quartz flashtube filled with xenon gas with full-width-half-maximum (FWHM) durations ranging from 2–5 milliseconds. It is the light output from this plasma arc that serves as the heat source in pulsed thermography NDE. Commercial power supply/flashlamp combinations from manufacturers such as Speedtron and BALCAR®, which were originally designed for professional photographers, are now used almost exclusively by practitioners of pulsed thermography NDE.

In configuring the flashlamps for pulsed thermography NDE, quasi-parabolic reflectors in symmetric pairs arranged about the IR camera typically house the flash lamps. As such, the flash lamps are generally placed a few feet away from the sample, so that a small sample positioned at the intersection of two flashlamp beam paths will be illuminated in an approximately uniform manner. This arrangement provides satisfactory uniformity as long as there is sufficient space to allow the lamps to be adequately far from the sample. However, since the intensity of light reaching the sample decreases as the inverse square of the distance between the lamp and the sample, practitioners often use several pairs of high-energy flashlamps and power supplies to compensate for the lost energy.

Several drawbacks result from the standard practice of using photographic equipment in pulsed thermography NDE. For example, the direct energy projected onto the sample by the plasma arc is much greater than the indirect energy projected by the reflector, so that the actual spatial temperature distribution at the sample surface may be quite non-uniform, with "hot spots" in the areas where the direct energy of the plasma arc was projected onto the sample. Invariably, in describing pulsed thermography, the use of a "brief, spatially uniform pulse of light" is mentioned; however, close scrutiny of the current practice employed in pulsed thermography NDE clearly shows that the generated light pulses are neither spatially uniform, nor brief, when considered on the scale of thermal diffusion times.

Although cameras operating at the standard (50/60 Hz) frame rate are adequate in most NDE applications, high speed cameras may be used in some particular NDE applications. However, high speed cameras are significantly more expensive and generally require some trade-off in pixel density (i.e. the pixel count must be reduced as the frame rate is increased, in order to maintain operation within a fixed bandwidth limit). Furthermore, IR cameras can be rendered ineffective by conventional thermal excitation schemes that are widely used because these schemes can cause causes detector saturation or nonlinear camera response (especially in the frames proximate to the excitation by the light pulse). As a result, true high speed, high resolution pulsed thermography NDE is rarely performed, and can only be done with extremely specialized (and expensive) equipment.

Even further, there are several negative consequences associated with the conventional pulsed thermography NDE, some of which are:

1. The equipment is large and cumbersome, and does not lend itself to applications where a small portable unit is to be deployed, such as aircraft inspection.

2. Although the FWHM of the flash pulse is in the 2–5 milliseconds range, there is also a substantial IR component to the flash that causes a significant afterglow effect that is typically 25–35 milliseconds in duration. Thus, the afterglow tends to cause the IR camera to saturate or yield a non-linear response.

3. The energy from the afterglow may mask weaker signals emitted from the sample that indicate features or defects residing near the surface of the sample under examination.

4. Although high-speed cameras at frame rates up to 1.5 kHz are commercially available, the performance of these cameras is not well integrated with to the characteristics of the off-the-shelf flashlamps described above. The duration of the flash and the subsequent tail tends to render the camera "blind" for several frames, so that data that corresponds to "near surface features" is lost.

5. Analysis of pulsed thermography data is generally performed on the time history of the sample surface temperature response as it returns to room temperature. However, as the temperature approaches ambient, noise effects become more pronounced and the signal to noise ratio decreases. As a result, it becomes difficult to detect deeper defect features, as weaker signals are masked by noise from the camera electronics or stray reflected radiation.

6. The light intensity at the sample surface is not uniform unless the sample is placed in the far field of the lamps.

Thus, a need exists for an improved pulsed thermography system that overcomes the deficiencies of off-the-shelf photographic products that were originally designed for commercial photographers.

SUMMARY OF THE INVENTION

According to one aspect of the invention, an add-on pulse controller device has been developed that serves as an accessory to popular high-energy flash supplies, such as, for example, Speedtron and BALCAR®. In operation, the add-on pulse controller device truncates thermographic imaging flash duration and adjusts the onset of flash timing to render precise control of flash timing characteristics.

According to another aspect of the invention, a portable pulsed thermography system is configured to provide high speed capability using a camera operating at the conventional (60 Hz) frame rate. The portable pulsed thermography system addresses the uniformity and duration of the flash illumination, as well as the placement and proximity of the flashlamp, and the method by which data is acquired and processed.

DESCRIPTION OF THE PREFERRED EMBODIMENT

Figure 1A:
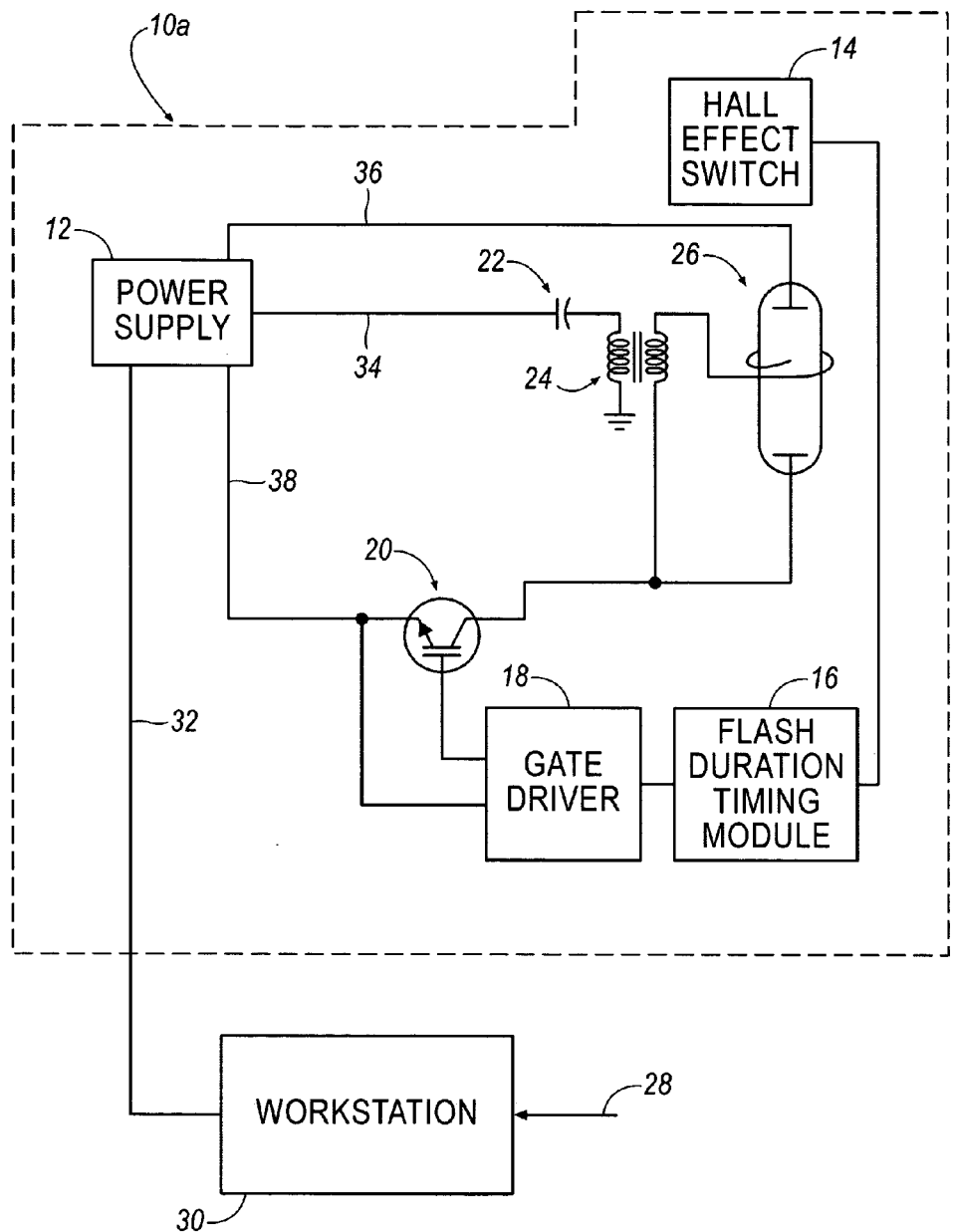
FIG. 1A illustrates a series pulse controller device according to an embodiment of the invention.
Figure 1B:
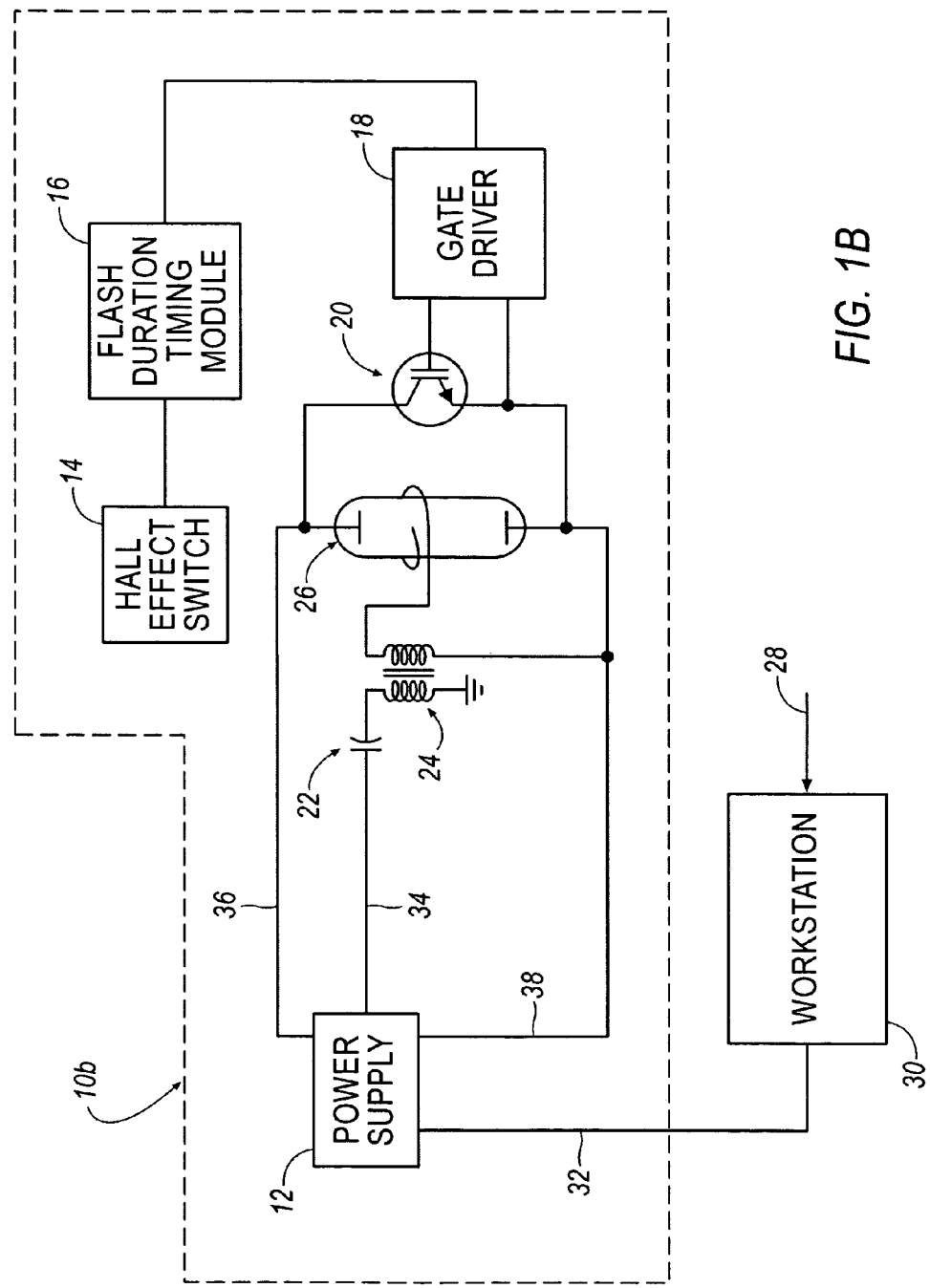
FIG. 1B illustrates a parallel pulse controller device according to another embodiment of the invention.

Referring to FIGS. 1A and 1B, an add-on pulse controller device is shown generally at 10a and 10b, respectively. As illustrated, the pulse controller device 10a is arranged in a series configuration, and the pulse controller device 10b is arranged in a parallel configuration. Each pulse controller device 10a, 10b is arranged to include a power supply 12, a Hall effect switch 14, a flash duration timing module 16, a gate driver 18, an Insulated Gate Bipolar Transistor (IGBT) 20, a power supply capacitor 22, a trigger transformer 24, and a flashtube 26.

As illustrated, a video synchronize signal 28 is fed into a workstation 30, such as a personal computer, that drives the power supply 12. In operation, when the workstation 30 issues a control signal over path 32 to the power supply 12, the power supply 12 issues a trigger pulse output signal (e.g. a 250 volt capacitive discharge pulse) over path 34 to the power supply capacitor bank 22, which excites the trigger transformer 24 to ionize the flashtube 26. The remaining two conductors 36, 38 extending from the power supply 12 are main power output lines. According to the illustrated embodiments of FIGS. 1A and 1B, the commencement of the trigger pulse output signal may be controlled, relative to the video signal 28 coming from the camera.

According to the first embodiment, the pulse controller device 10a is arranged such that the IGBT 20 is located in series with the flashtube 26. Thus, the current flow through flashtube 26 can be quickly interrupted to thereby terminate a plasma discharge within flashtube 26. According to the embodiment of FIG. 1B, the pulse controller device 10b is arranged in parallel to provide an alternate current path. As such, solid state IGBT 26 can be closed to shunt current flow away from the flashtube 26. Although each embodiment accomplishes the same effect, the series pulse controller device 10a is considered to be a preferred embodiment because it uses energy stored in the power supply 12 more efficiently (i.e., only the amount of energy needed for the flash pulse is drained from the power supply capacitor 22). As a result, it is possible to recharge the power supply capacitor 22 very quickly when short flash pulses are employed, thereby permitting use of the flashlamp 26 in a fast, repetitive mode. Even further, although each embodiment of the pulse controller device 10a, 10b includes an IGBT 20, it will be appreciated that the invention is not limited to an IGBT 20, and that other devices could be employed to accomplish the same result. For example, such devices may include, but are not limited to Gate Turnoff Thyristors (GTO), integrated Gate Commutated Thyristors (IGCT), or the like.

Figure 2:
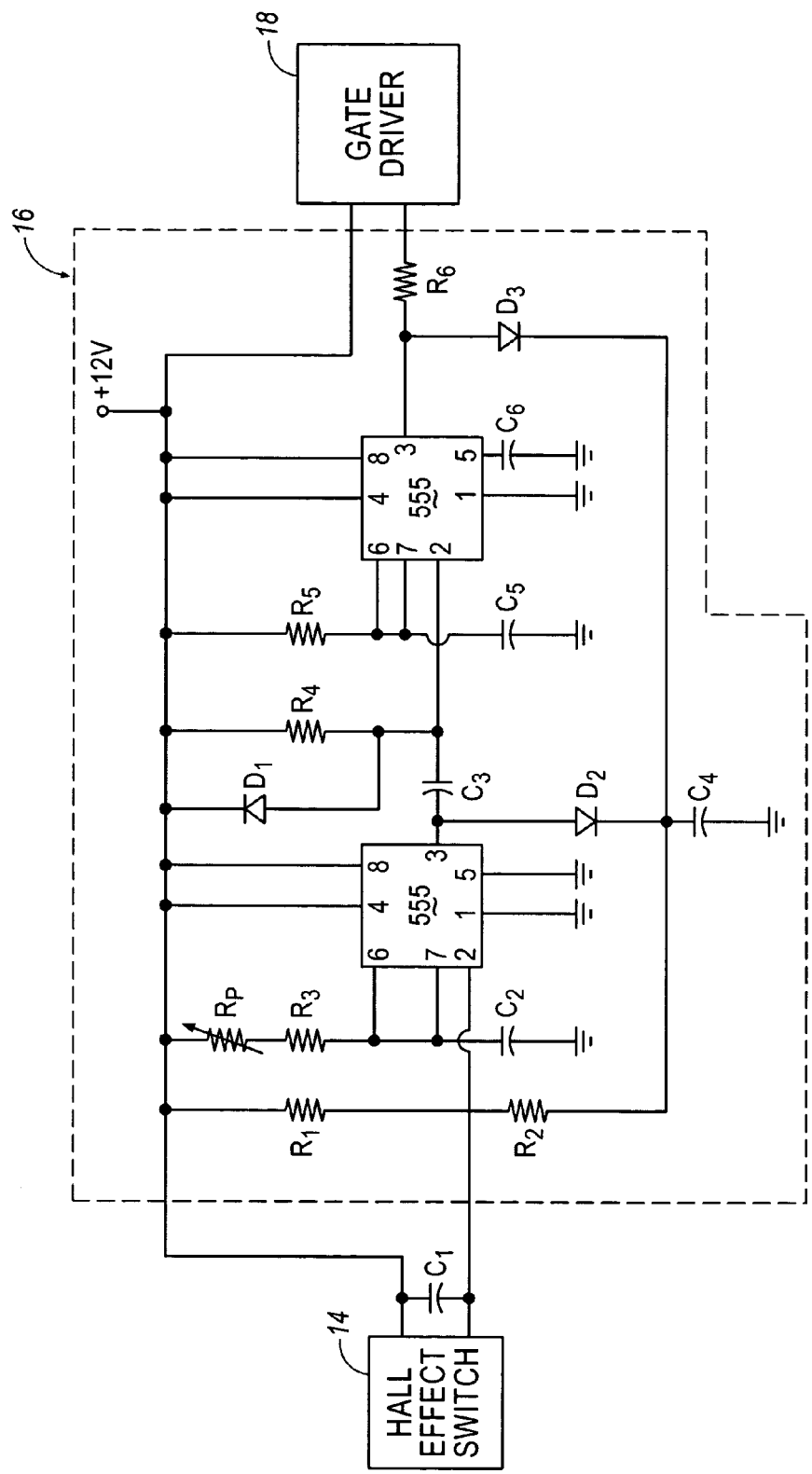
FIG. 2 illustrates a flash pulse timing module according to an embodiment of the invention.

Referring to FIG. 2, each embodiment 10a and 10b includes a flash duration timing module 16. The flash duration timing module includes a pair of 555 timer chips. In an alternative embodiment, one half of a 556 dual timer (not shown) may be employed, if desired. According to an embodiment of the invention, a first capacitor, $C_1$, located between the Hall effect switch 14 and flash duration timing module 16 may have a value of 0.1 μF. As also illustrated in FIG. 2, the flash duration timing module 16 may include, according to an embodiment of the invention, capacitors, $C_2$–$C_6$, having values equal to 0.1 μF, 0.01 μF, 47F, 1 μF, and 0.01 μF, respectively. The flash duration timing module 16 may also include, according to an embodiment of the invention, a 50 kΩ potentiometer, $R_P$, and resistors, $R_1$–$R_6$, having values equal to 24 kΩ, 10 kΩ, 4.53 kΩ, 2.2 kΩ, 90.9 kΩ, and 180 kΩ, respectively. The flash duration timing module 16 may also include, according to an embodiment of the invention, 1N4148 diodes, $D_1$–$D_3$. In operation, the Hall effect switch 18 magnetically senses the onset of the current flow through in the flashtube 26 via a magnetic coupling to the high tension lead of the flashtube 26. As such, when the flashtube 26 starts to produce light, it draws a large amount of current from the power supply capacitor bank 22.

Although the function of the flash duration timing module 16 shown in FIG. 2 is implemented in hardware, one skilled in the art will readily recognize that such a function can also be carried out in software, for example software implemented in workstation 30. If a software embodiment of timing module 16 is implemented, the hardware associated with switch 14 and module 16 is eliminated.

Figure 3:
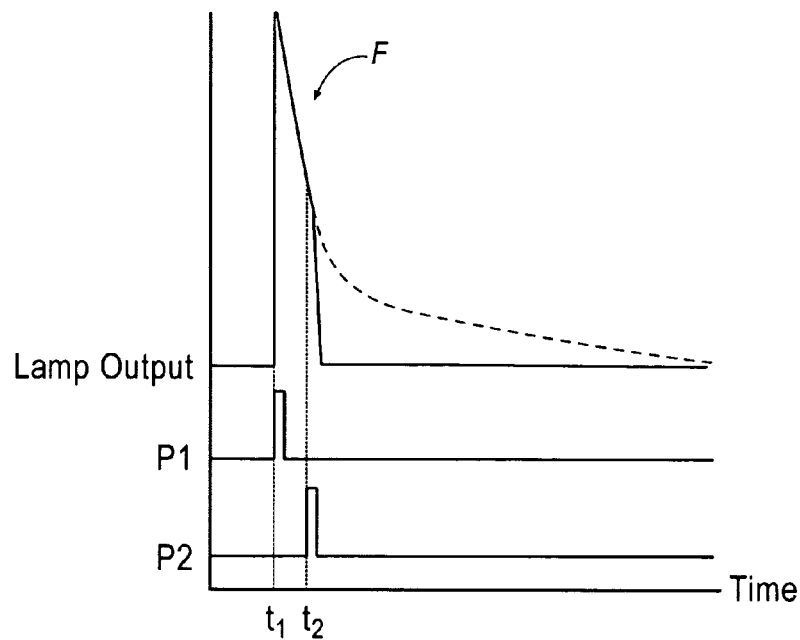
FIG. 3 illustrates a pulse controller timing diagram derived from the pulse controller device according to FIG. 1A or 1B.
Figure 4:
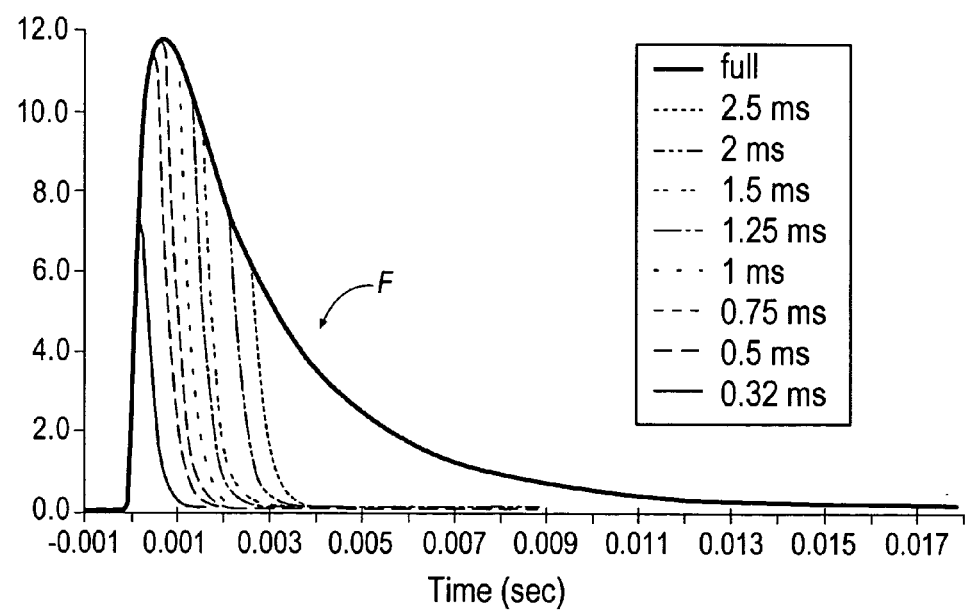
FIG. 4 illustrates a flash pulse duration reduction timing diagram as applied to the pulse controller device according to FIG. 1A or 1B.
Figure 5:
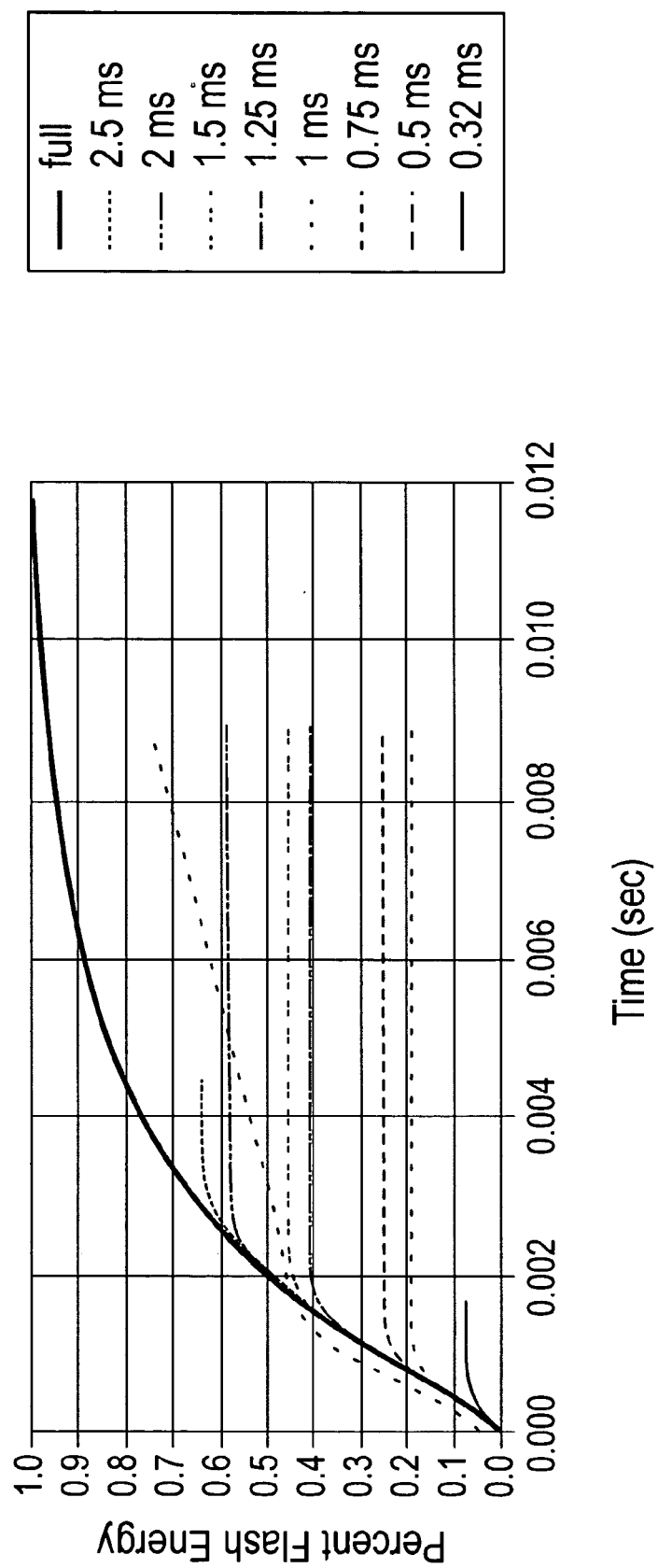
FIG. 5 illustrates a timing diagram of integrated flash energy in view of decreasing flash duration.

In general, to operate the pulse controller device 10a, 10b, a user interface is provided and integrated into an NDE software package that analyzes and initiates acquisition of data related to a sample to be evaluated. Each pulse controller device 10a, 10b controlled by the software is based on a standard flash power supply 12 and a linear xenon flashtube 26. Referring to FIG. 3, when a pulse, P1, is communicated over path 32 from the workstation 30 to the power supply 12, a plasma discharge (i.e. lamp output) is triggered, which initiates a flash, F, from the flashtube 26. Then, at a predetermined time interval (commencing at time, $t_2$), flash duration timing module 16 sends pulse, P2 to gate driver 18. Gate driver 18 operates IGB720 to cause the current through flashtube 26 to cease the flash, F. As seen in FIGS. 4 and 5, the duration and strength of the flash, F, may be reduced and substantially truncated at any desirable time ranging, for example, from 0.32–2.50 milliseconds. $R_P$ is effective for adjusting the time range.

Figure 6:
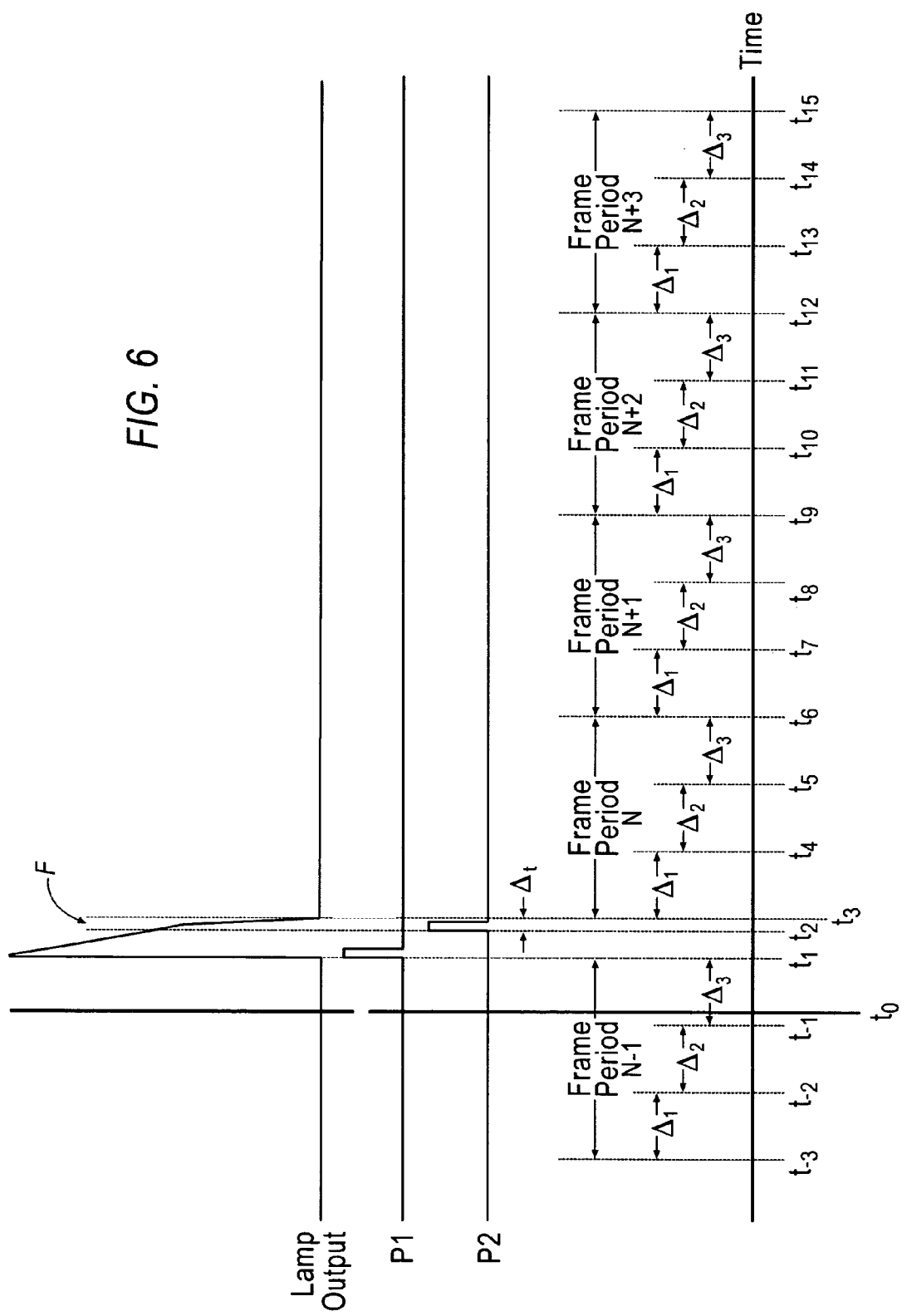
FIG. 6 illustrates another pulse controller timing diagram including a plurality of frame periods.

Referring to FIG. 6, several frame periods, each of which contain sub-periods $\Delta_{1-\Delta 3}$, for the capturing of thermographic images of a sample are shown in reference to the timing diagram illustrated in FIG. 3. Each frame period is defined to include a capture/integrate sub-period, $\Delta_1$, a hold/read sub-period, $\Delta_2$, and a wait period, $\Delta_3$. According to one embodiment of the invention, the frame period and capture/integrate sub-period, $\Delta_1$, of a 60 Hz. camera is approximately 16.66 milliseconds and 1 to 3 milliseconds, respectively. Although the sub-periods are shown to include substantially similar durations, the invention is not limited to the durations as shown, and each sub-period, $\Delta_{1-\Delta 3}$, may include any desirable, non-uniform duration.

As shown, a pre-flash frame period, N−1, occurs at some time prior to the flash, F. Flash, F, starts in synchronization with the first pulse, P1. The frame period, N, which is shown from $t_3$ to $t_6$ does not commence until after a delay period, $\Delta_T$, has ceased. As illustrated, the delay period, $\Delta_T$, commences when the second pulse, P2, commences at $t_2$. Thereafter, the delay period, $\Delta_T$, terminates at $t_3$. As such, the frame period, N, occurring from $t_3$ to $t_6$ is set to start when the current driving the flash, F, has completely died-out. However, it will be appreciated that the delay period, $\Delta_T$, may be adjusted in duration such that time $t_3$ is synchronized with a moment when the flash, F, has not died-out. Thus, the invention provides for the ability for one to adjust the duration of the delay period, $\Delta_T$, and to adjust the start of the first post-flash frame period, N. Programming of the delay period, $\Delta_T$, may be accomplished by software in the workstation 30, the hardware of the timing module 16 (using $R_p$), or by settings of the camera.

Figure 7A:
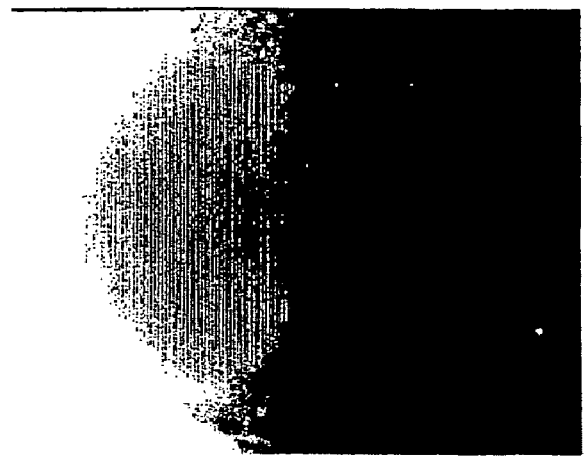
FIG. 7A illustrates an image of a sample taken at full power with a conventional flash duration period.
Figure 7B:
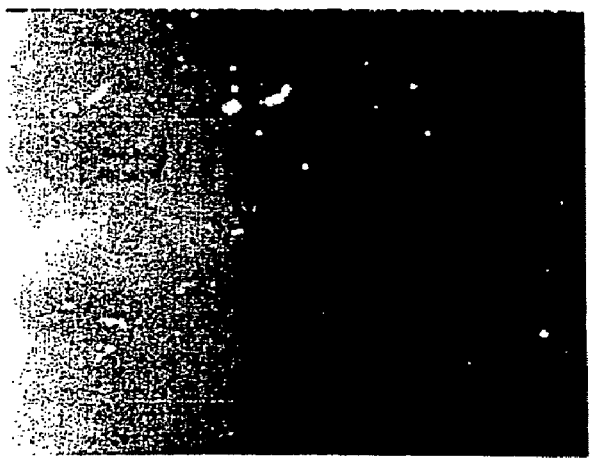
FIG. 7B illustrates an image of the sample of FIG. 7A taken at full power with a reduced flash duration period as applied to the pulse controller device of FIG. 1A or 1B.

As a result, an image may be arrived at when full power is used during a reduced flash duration. As illustrated in FIG. 7A, a normal flash duration having a period of approximately 17 milliseconds contains less clarity than a truncated flash duration period of approximately 2.74 milliseconds, as illustrated in FIG. 7B. Thus, the ability to control the precise commencement and duration of the flash excitation enables several improvements to the conventional pulsed thermography process. The pulse of shorter duration allows a clearer delineation between the stimulus (i.e., flash) and response (i.e., sample heating and subsequent cooling), as these often overlap using conventional flash excitation.

The truncated flash, F, enhances the performance of signal enhancement techniques, such as, for example, Thermographic Signal Reconstruction (TSR), as described in United States Published Patent Application No. 2002-0172410A1. The TSR technique is based on the characteristics of the natural logarithm of the post-flash temperature vs. time behavior of each pixel in the image. In principle, every pixel in a defect-free sample exhibits ln(T) vs. ln(t) behavior as a consequence of 1-dimensional diffusion that occurs as the sample cools. The ideal slope of the line that obtains is (−0.5) although the initial few frames during and after the flash typically deviate significantly from ideal behavior because of the timing problems associated with the flash. Thus, the use of a truncated flash and precise flash timing permits mathematical correction of the ln—ln plot of each pixel so that behavior is much closer to the ideal image. This results in a reduction in discontinuities in the time derivative of early frames in the sequence, which significantly improves the TSR calculation (since fewer higher order terms in the polynomial are required).

Even further, it will be appreciated that the optical excitation from the flashlamp 26 could be replaced by many other methods, such as, for example, hot air, hot water, cold air, or the like; however, the use of light offers a unique opportunity, which the present invention exploits. The light pulse from the flashlamp 26 contains spectral components that extend beyond the visible range. In fact, during the actual flash, there is a significant IR component that can adversely affect the thermography result, in that the IR radiation may be reflected off of the surface of the sample, and propagate into the camera lens. Since thermography is based on using emitted radiation from the sample, this reflected signal is undesirable. Consequently, the video frame(s) acquired during the flash event is often saturated, or the recorded intensity exceeds the camera calibration range, because of the excessive IR flux into the camera. Since the flashlamp 26 and fixture remain hot for a brief period after the flash event, and thus, continue to radiate relatively large amounts of IR energy, the first few frames after the flash may also be saturated or be beyond the calibration range, which would thereby render an inaccurate result. This problem is exacerbated when the flash occurs during the actual integration time of the camera. Accordingly, as a result of the present invention, these problems can be eliminated by reducing the flash duration, and by adjusting the commencement and duration of the flash to guarantee that the flash does not occur during the integration time. In fact, it is possible to set the flash duration and camera offset (with respect to integration time) so that there is no saturation in any frame, but that the initial frame shows the sample illuminated by some portion of the post-flash IR radiation. In this very early period, the image is essentially a reflected IR image of the sample surface, as opposed to the subsequent images that are the result of emitted IR radiation, which are affected by subsurface features in the sample. Typically, the image during the flash is discarded in thermographic NDE. Using the present invention, it is recognized that the t=0 image (during the flash) is generated using an entirely different mechanism (i.e. IR reflection) than images acquired later in the cooling sequence, which are the result of radiation from the surface of the sample.

The reflected image may be useful in several situations, particularly in the case of materials including those that have a top layer that is fully transparent, semi-transparent, or optically opaque. If the top layer is optically opaque, the top surface appears to be semi-transparent in some portions of the infrared spectral band (e.g. many paints, primers and ceramic coatings such as the thermal barrier coatings used in turbine generators and engines) when exposed to a high flux, direct illumination. In such cases, the t=0 image may be used to view features such as markings, scratches, dirt or corrosion that resides under the coating layer, but on the substrate surface. The rest of the data sequence may be used to image, detect, or measure subsurface features, using a method such as TSR.

Figure 8:
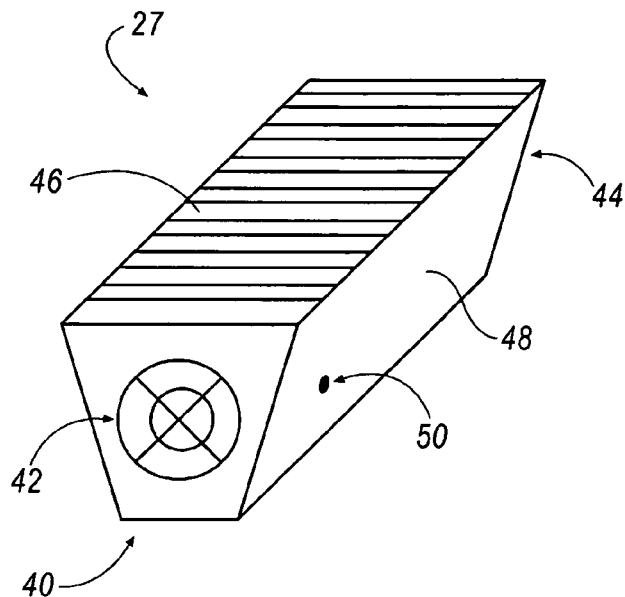
FIG. 8 illustrates a perspective view of a flashlamp of FIG. 1A or 1B according to an embodiment of the invention.
Figure 9:
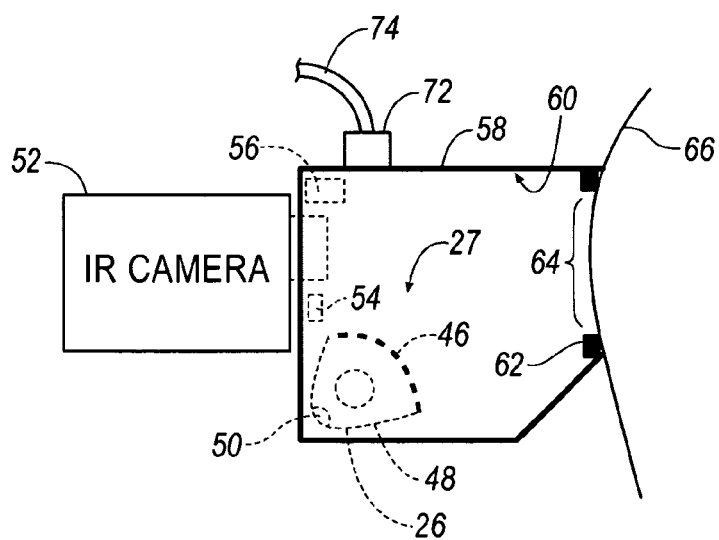
FIG. 9 illustrates a side schematic view of a pulsed thermography system including the flashlamp of FIG. 8 according to an embodiment of the invention.
Figure 10:
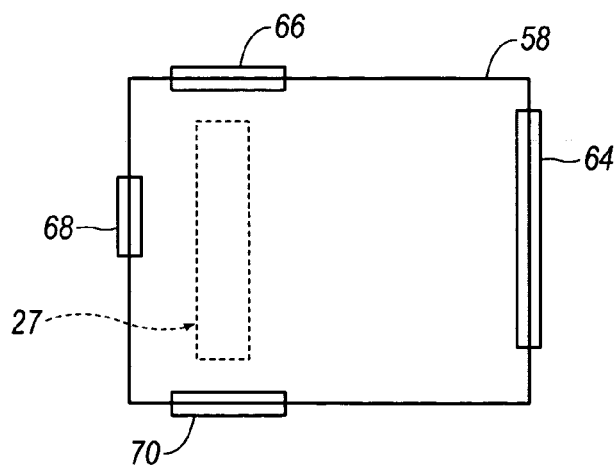
FIG. 10 illustrates a top schematic view of the pulsed thermography system according to FIG. 9.

Referring to FIG. 8, the flashlamp assembly 22 is described in greater detail. As illustrated, the flashlamp assembly 22 includes an air exhaust side 40 including a flashlamp fan 42 and an opposing air intake side 44 with an flashlamp intake port (not shown). The flashlamp assembly 22 also includes a holographic diffuser 46, a reflector 48, and a photodiode with a pinhole aperture, which is seen generally at 50, that is disposed about the reflector 48. Referring to FIGS. 9 and 10, the flashlamp assembly 22, along with an IR camera 52, IR illuminator 54, and photodiode 56, are located within a hood enclosure 58. The hood enclosure 58 includes reflective interior walls 60, contact switches 62, and a sample aperture 64 to permit thermographic evaluation of a sample 66. The hood enclosure 58 also includes an air intake aperture, a camera lens aperture, and an exhaust fan aperture, which are generally designated at 66, 68, and 70, respectively.

Accordingly, light from the flashtube 26 is transmitted through the holographic diffuser either directly or indirectly (i.e. after reflecting from the reflector walls 60). The diffuser creates a more uniform spatial distribution of light intensity at the sample 66. The diffuser 46 is attached to the reflector 48 to create a light-proof seam so that light must pass through the diffuser 46 if it is to reach the sample 66. To maintain steady-state temperature of the flashtube 26, and to avoid convective heating of the sample 66, the exhaust fan 42 draws air through from the intake port and across the flashtube 26. The photodiode with pinhole aperture 50 is placed behind the flashtube 26 in the reflector 48, to measure the visible light output from the flashtube 26. The second photodiode 56 is mounted in a small collimator telescope and is placed along the back wall of the hood enclosure 58 in order to measure the light that is reflected off of the sample 66. Both photodiodes 50 and 56 are gated to collect light for a brief period during the plasma discharge. The photodiodes 50, 56 are controlled and read out by a micro-controller 72 that is attached to the enclosure 58. The micro-controller 72 calculates the ratio of reflected light to flash output, and transmits this number to the workstation 30 by serial data link 74.

Thus, the present invention controls the duration of the flash and the precise timing of the onset of the flash with respect to the camera video frame. The approach to controlling the duration of the flash is to use standard commercial flashlamps and power supplies, but with an intermediate device 10a, 10b that truncates the flash pulse after the desired duration. Truncation of the flash pulse in this manner also reduces the duration of the afterglow, and allows detection of near surface events that are normally masked by the flash. The flash truncation device 10a, operates in a series mode that does not cause the power supply capacitor 22 to be discharged completely, so that as the flash duration shortens, so does the capacitor recharge time (i.e., since a shorter flash drains less energy from the power supply capacitor 22). As a result, it is possible to operate in a repetitive flash mode, using the very fast recycle time afforded by the present invention.

The present invention also allows precise adjustment of the timing of the onset of the flash, so that the flash may be set to occur precisely between frames, or at a specific time during a frame. It is also possible to conduct quasi high-speed imaging with a camera operating at standard frame rates by acquiring several flash excitation sequences with the flash timing slightly offset in each sequence. When the data from all sequences are combined, the result is effectively a single flash sequence with much finer time resolution than the camera is capable of providing.

The present invention also allows employment of a single flashlamp assembly 27, or a combination of flashlamps, to provide a brief uniform pulse in a form factor that is small enough for use in portable applications. The flashlamp 26 is housed in a reflector 48 that is sealed so that no radiation can leak out in the direction of the sample 66. Light emerging from the reflector 48 must pass through a holographic diffuser 46, which distributes the light evenly over the target area of the sample 66 that is regulated by the width of the sample aperture 64. The diffuser 46 is flexible, and can be formed to optimize the distribution of the beam at the surface of the sample 66 positioned about the sample aperture 64. Although the same effect could be accomplished with lenses, the lens would pass either visible or infrared radiation, but not both, unless extremely expensive custom optical materials were used. However, lens incorporated into the invention as described above would have to be relatively larger, add weight, require addition real estate, require precise placement, and would require an entire field of output of the flashlamp. Conversely, the diffuser 46 is highly flexible, simple to place, includes minimal transmission loss, and would not require precise alignment and precision. Since the flash fixture is sealed, warm air is prevented from heating the evaluated surface of the sample 66, which would otherwise corrupt thermographic measurements. As such, the heated air is drawn away from the flashtube 26 by the exhaust fan 42 proximate the air exhaust side 40 of the reflector 48. The exhaust fan 42 draws air in through an intake port on the air intake side 44 of the reflector 48, and pulls it across the flashtube 26 in order to cool the flashtube 26. The entire flash assembly 27 is housed in a lightweight (preferably constructed with aluminum or composite materials) hood enclosure 58 with reflective walls 60, an aperture 68 for the IR camera lens, and an exit aperture 64 that matches the filed of view of the IR camera optics. The reflector 48, diffuser 46, and the reflective walls 60 are considered to be part of the optical system, and are arranged to allow optimal uniformity at the exit aperture 64 of the hood enclosure 58, where the surface of the sample 66 is presented to the IR camera 52.

In most applications of pulsed thermography, little attention is paid to the amplitude of the flash output, or the precise amount of energy that is delivered to the surface of the sample 66. For industrial applications, where hundreds, or even thousands of identical parts are to be inspected with an automated system, it is important to know that flash parameters fall within an acceptable range, so that defect-free parts are not mistakenly rejected because of a missed flash or improperly orientated sample 66. Commercial, off-the-shelf photographic equipment does not typically provide such information. The present invention provides feedback regarding flash operation through the use of photodiodes 50, 56 and a micro-controller 72. The photodiodes 50, 56 are typically operated in reverse bias mode, to allow high-speed operation, and they are gated so that acquisition coincides with the occurrence of the flash. Both photodiodes 50, 56 may be configured to operate as either peak detectors, or to integrate over a specified period of time. The photodiode 50 is placed behind the flashtube 26, in order to monitor the visible light output of the flash. A pinhole aperture, and if necessary, a neutral density filter, are placed between the flashtube 26 and photodiode 50, as the light signal from the flash is typically large and would saturate the unprotected photodiode 50. Since the relative positions of the flashtube 26 and photodiode 50 are fixed, it is possible to calibrate the output of the photodiode 50 using a more sophisticated laboratory radiometer, so that the amount of energy per flash could be assessed during inspections by monitoring photodiode current or voltage.

The second photodiode 56 is designed to measure the reflectivity of the sample 66, relative to a test sample with the same shape and surface finish as the subsequent parts to be inspected. Since in an industrial inspection, the parts under test would typically be automatically placed in precisely the same position (i.e., distance and orientation) with respect to the enclosure hood 58, the amplitude of reflected light off the sample and into photodiode 56 should be nearly constant. The input to photodiode 56 may be the reflection of the flash off the sample 66 and into the photodiode 56 should be nearly constant. The input to the photodiode 56 may be the reflection of the flash off the surface of the sample 66, in which case, acquisition would be gated to coincide with the occurrence of the flash, and the photodiode 56 would be mounted in a collimator tube or telescope, to insure that only light reflected off the surface of the sample 66 and not the direct output of the flashtube 26 is detected. Alternately, an LED or laser diode may be placed in the hood enclosure 58 and configured to bounce light off the surface of the sample 66 and into the photodiode 56. In this embodiment, it is not necessary to gate acquisition, although it may be desirable to modulate the source so that stray light can be rejected. Accordingly, it is possible to calibrate the reflectivity measurement against samples of known reflectivity. Both photodiodes 50, 56 are controlled and read out by the micro-controller 72, which is interfaced to the workstation 30. If the photodiode 50 and/or the photodiode 56 are reading, or the ratio of the photodiode 50 to the photodiode 56 deviates from the baseline performance established with the test sample, an alarm signal would be sent to the workstation 30 to indicate that the inspection for that part was not valid.

One additional feature that serves both process control and safety is a contact switch 62 (or multiple switches). These are placed at the front of the hood enclosure 58 to ensure that a sample 66 is in place before a flash is executed. This protects personnel in the area from inadvertent expose to the flash when the exit aperture 64 of the hood enclosure 58 is not blocked by the sample 66.

In conventional thermography, features on the surface of the sample 66, such as decals, appliques, dirt, oil, or paint smears may appear in the resulting images, in which case, they can be mistaken for subsurface features. Although standard practice dictates that images of the surface before flash heating should be acquired, details of the sample surface may not be detectable, or they be extremely weak in the pre-flash images due to the relatively low flux radiation at room temperature compared to the post-flash flux. This is because the emitted energy from the sample surface at ambient temperature is masked by infrared energy from background sources (e.g. the flashlamp fixture or even humans in the area if a enclosure hood 58 is not used). The present invention uses a small, active IR illuminator 54 to illuminate the surface of the sample 66, so that surface features can be clearly viewed, and compared to features that appear in the post-flash images. We have found the miniature blackbody sources from Ion-Optics to be particularly effective for this purpose, as they are small, they run on low current, and they do not generate excessive convective heating in the hood enclosure 58. The IR illuminator 54 may be used in any of several ways:

a) for a portion of the pre-flash period;
b) for the entire pre-flash period;
c) for the entire acquisition sequence (before, during and after flash); and
d) after the acquisition to view the surface (or as part of a marking scheme, such as Data Integration and Marking).

The IR illuminator 54 operates at very low energy, which is reflected off the surface of the sample 66. It causes very little heating of the sample surface, and has negligible effect on the normal pulsed thermography process.

Figure 11:
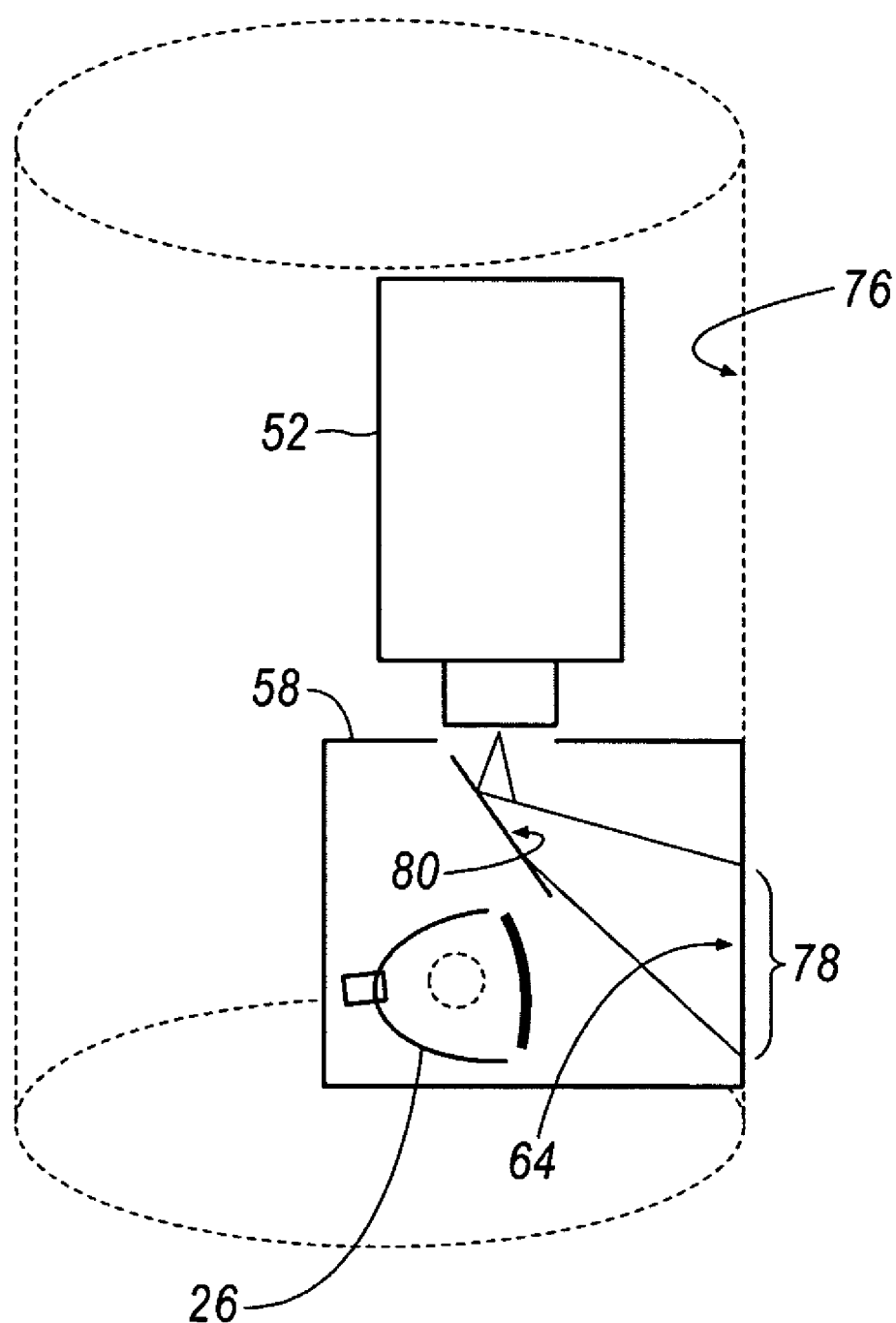
FIG. 11 illustrates a side schematic view of a pulsed thermography system including the flashlamp of FIG. 8 according to another embodiment of the invention.

Referring to FIG. 11, in some inspection applications, it may be necessary to fit the apparatus into a confined space, for example, when inspecting the inner surface of a pipe 76. In such cases, the above-described equipment shown in FIGS. 8–10 can be configured in a periscope arrangement, where the camera 52 view the sample surface 78 after reflection off of a front surface of a mirror 80. The mirror 80 is arranged to cover the field of view defined by the exit aperture 64 of the hood enclosure 58. Since the mirror 80 is not necessarily orientated at a 45-degree angle to the optical axis of the camera 52, some distortion of the resulting image is likely to occur. However, the amount of distortion is fixed, and can be corrected by anamorphic mapping of the images in software once they have been acquired.

Accordingly, the pulse controller device 10*a*, 10*b* provides an additional degree of control over the flash, F, by allowing adjustment of the time at which the flash, F, occurs, relative to the vertical sync signal of the previous frame. This allows the flash, F, to occur at any time in the video frame (e.g. during the vertical sync, in the middle of the frame, correlated to a particular horizon line, or to an external triggering event). It is also possible to configure flash triggering so that several consecutive flash excitation/data acquisition sequences occur, but with the timing of flash initiation progressively delayed with each repetition. In this case, the multiple sequences can be combined into a single sequence with higher time resolution than the actual frame rate of the camera, so that quasi high-speed thermographic inspection can be achieved with a camera operating at a standard (e.g. 60 Hz) frame rate.

While the invention has been specifically described in connection with certain specific embodiments thereof, it is to be understood that this is by way of illustration and not of limitation, and the scope of the appended claims should be construed as broadly as the prior art will permit.

The invention claimed is:

1. A pulse controller device used for controlling the excitation of a heat source used in thermographic imaging, comprising:

a power supply, a heat source coupled to the power supply, a device coupled to the power supply for signaling the power supply to deliver electrical power to the heat source, a sensor for sensing the delivery of electrical power to the beat source, a flash duration module coupled to said sensor for defining a duration of time associated with the delivery of electrical power to the heat source, a gate device coupled to said heat source and coupled to said flash duration module for gating the electrical power utilized by the beat source.

2. The device of claim 1, said sensor is a Hall effect sensor.

3. The device of claim 2, wherein said Hall effect sensor is magnetically coupled to an electrical conductor extending between said heat source and said power supply.

4. The pulsed thermography system according to claim 2 further comprising a microcontroller attached to the hood enclosure that controls the pinhole photodiode disposed about the reflector and the photodiode positioned in the hood enclosure, wherein the microcontroller calculates a ratio of reflected light to the photodiodes and transmits the calculated ratio to the workstation by a serial data link.

5. The device of claim 1, wherein said flash duration module includes first and second hardware timers wherein an output pulse of the first timer is used as an input pulse to the second timer.

6. The device of claim 1, wherein duration of time defined by said flash duration module is adjustable in the range of approximately 0.32 milliseconds to approximately 17 milliseconds.

7. The device of claim 1, wherein said gate device is electrically connected in series with said heat source.

8. The device of claim 1, wherein said gate device is electrically connected in parallel with said heat source.

9. The device of claim 1, wherein the signaling device coupled to power supply includes a work station.

10. A pulsed thermography system, comprising:
a hood enclosure including at least one aperture for evaluation of a sample surface; and
a flashlamp and at least a portion of an infrared camera disposed within the hood enclosure to conduct thermographic evaluation of the sample surface wherein the flashlamp further comprises a photodiode to measure the visible light output from the flashlamp,
wherein the photodiode is mounted in a collimator telescope and positioned along a rear wall of the hood enclosure to measure light that is reflected off of the sample surface.

11. The pulsed thermograph system according to claim 10, wherein the hood enclosure includes reflective interior walls.

12. The pulsed thermography system according to claim 11, wherein the flashlamp further comprises a holographic diffuser that creates a more uniform spatial distribution of light intensity at the sample surface by either directly transmitting or redirecting light that reflects off the reflective interior walls.

13. The pulsed thermography system according to claim 12, wherein the flashlamp further comprises a reflector that directs light from the flashlamp through the diffuser prior to reaching the sample surface.

14. The pulsed thermography system according to claim 12, wherein the holographic diffuser is flexible.

15. The pulsed thermography system according to claim 10, wherein the at least one aperture is further defined to include
a sampling aperture that permits evaluation of the sample surface,
a camera lens aperture to permit thermographic imaging of sample surface by the infrared camera,
an air intake aperture and an air exhaust aperture positioned in axial alignment with an air intake port and exhaust fan of the flashlamp to permit cooling of the flashlamp.

16. The pulsed thermography system according to claim 15 further comprising contact switches located about the perimeter of the sampling aperture to ensure that the surface being sampled is in place before the flashlamp is activated.

17. The pulsed thermography system according to claim, 10, wherein the portion of the infrared camera disposed within the hood enclosure is a lens of the infrared camera.

18. The pulsed thermography system according to claim 10 further comprising a minor positioned at an off-normal angle with respect to the camera lens to evaluate a non-planar sample surface.

19. The pulsed thermography system according to claim 18, wherein the non-planar sample surface is a portion of a tubular surface.

20. The pulsed thermography system according to claim 10, wherein the flashlamp is housed in a sealed flash fixture such that warm air is prevented from heating the sample surface.

21. A method for thermographically evaluating a sample, comprising the steps of:
prior to capturing thermographic images during a cooling sequence in a first data set, pulsing light from a flashtube;
capturing infrared radiation that is reflected from a sample in a preliminary data set; and
on the basis of the reflected infrared radiation, evaluating surface features of a substrate of the sample located beneath a coating layer.

22. The method according to claim 21, wherein the coating layer is optically opaque, but appears to be semi-transparent when exposed to the infrared light from the flashtube, wherein the infrared light from the flashtube is a high flux direct illumination.

23. The method according to claim 21, wherein the coating layer includes paint, or a primer.

24. The method according to claim 21, wherein the coating layer includes a thermal barrier ceramic coating.

25. A method for thermographically evaluating a sample, comprising the steps of:
conducting a quasi high-speed thermographic imaging with a camera by acquiring several flash excitation sequences with a flash timing progressively delayed in each flash excitation sequence; and
combining the several flash excitation sequences into a single flash sequence having a finer time resolution than that provided by the camera.

26. A method for thermographically evaluating a sample, comprising the steps of:
initiating and subsequently truncating the duration of a flash sequence;
setting a delay period that starts with the instance of the flash truncation; and
at the end of the delay period, initiating at least one frame period for thermographically imaging a sample,
wherein the delay period ends when the truncation of the flash has substantially died-out.

27. The method according to claim 26, wherein the at least one frame period is defined by a capture/integrate sub-period, a hold/read sub-period, and a wait period.

28. The method according to claim 26 further comprising the step of initiating at least one pre-flash frame period occurs prior to the initiating of the flash.

29. A method for thermographically evaluating a sample, comprising the steps of:

initiating and subsequently truncating the duration of a flash sequence;

setting a delay period that starts with the instance of the flash truncation; and at the end of the delay period, initiating at least one frame period for thermographically imaging a sample, wherein the delay period ends prior to the dying-out of the flash.

30. The method according to claim 29, wherein the at least one frame period is defined by a capture/integrate sub-period, a hold/read sub-period, and a wait period.

31. The method according to claim 29 further comprising the step of initiating at least one pre-flash frame period occurs prior to the initiating of the flash.

* * * * *

UNITED STATES PATENT AND TRADEMARK OFFICE
CERTIFICATE OF CORRECTION

PATENT NO. : 7,186,981 B2  Page 1 of 1
APPLICATION NO. : 10/902225
DATED : March 6, 2007
INVENTOR(S) : Steven Shepard It is certified that error appears in the above-identified patent and that said Letters Patent is hereby corrected as shown below:

In Claim 1, column 10, line 64, please change "beat" to --heat--.

In Claim 1, column 11, line 3, please change "beat" to --heat--.

In Claim 2, column 11, line 4, please insert --wherein-- before "said".

In Claim 18, column 12, line 9, please change "minor" to --mirror--.

Signed and Sealed this

First Day of May, 2007

JON W. DUDAS
*Director of the United States Patent and Trademark Office*